United States Patent
Zeller et al.

(10) Patent No.: US 12,189,013 B2
(45) Date of Patent: Jan. 7, 2025

(54) MAGNETIC RESONANCE IMAGING WITH A DYNAMIC DIFFUSION-WEIGHTING

(71) Applicant: Siemens Healthcare GmbH, Erlangen (DE)

(72) Inventors: Mario Zeller, Erlangen (DE); Adam Kettinger, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 168 days.

(21) Appl. No.: 17/950,980

(22) Filed: Sep. 22, 2022

(65) Prior Publication Data

US 2023/0098417 A1    Mar. 30, 2023

(30) Foreign Application Priority Data

Sep. 24, 2021  (EP) .................................. 21198721

(51) Int. Cl.
*A61B 5/0205*    (2006.01)
*A61B 5/055*    (2006.01)
*G01R 33/48*    (2006.01)
*G01R 33/563*    (2006.01)
*G06N 3/08*    (2023.01)

(52) U.S. Cl.
CPC ...... *G01R 33/56341* (2013.01); *A61B 5/0205* (2013.01); *A61B 5/055* (2013.01); *G01R 33/4818* (2013.01); *G06N 3/08* (2013.01)

(58) Field of Classification Search
CPC ............ G01R 33/56341; G01R 33/543; G01R 33/56308; A61B 5/0205; A61B 5/055
See application file for complete search history.

(56) References Cited

U.S. PATENT DOCUMENTS

| 2013/0338486 A1 | 12/2013 | Huang |
| 2023/0093079 A1 | 3/2023 | Zeller et al. |

OTHER PUBLICATIONS

Frost, Robert et al.; "3D Multi-Slab Diffusion-Weighted Readout-Segmented EPI with Real-Time Cardiac-Reordered k-Space Acquisition," Magnetic resonance in medicine; vol. 72; No. 6; pp. 1565-1579; 2013.
Wiggers diagram—showing the cardiac cycle events occuring in the left ventricle; File name: Wiggers Diagram 2.svg; https://commons.wikimedia.org/wiki/File:Wiggers_Diagram_2.svg; 2016.

(Continued)

*Primary Examiner* — Joseph M Santos Rodriguez
*Assistant Examiner* — Tommy T Ly
(74) *Attorney, Agent, or Firm* — Banner & Witcoff Ltd.

(57) ABSTRACT

In a method for diffusion-weighted MR-imaging of an object, which undergoes a cyclic motion, a first sub-period type of the cyclic motion is predicted for a first acquisition timeframe, where the first sub-period type corresponds to one of two or more predefined characteristic types of sub-periods of the cyclic motion. A first amount of diffusion-weighting may be selected based on the first sub-period type. A first MR-acquisition may be carried out during the first acquisition timeframe, where a diffusion-weighting according to the first amount of diffusion-weighting is applied. An MR-image of the object is generated based on MR-data including a first MR-dataset obtained as a result of the first MR-acquisition.

15 Claims, 4 Drawing Sheets

(56) References Cited

OTHER PUBLICATIONS

Samantha J. Holdsworth et al: "Robust GRAPPA-Accelerated Diffusion-Weighted Readout-Segmented (RS)-EPI"; Magnetic Resonance in Medicine; vol. 62; No. 6; pp. 1629-1640; XP055388894; US; ISSN: 0740-3194; DOI: 10.1002/mrm.22122; Dec. 1, 2009.
Ayush Singh et al. "Deep Predictive Motion Tracking in Magnetic Resonance Imaging: Application to Fetal Imaging," ARXIV.ORG; Jun. 7, 2020 (Jun. 7, 2020); XP081680163.

MAGNETIC RESONANCE IMAGING WITH
A DYNAMIC DIFFUSION-WEIGHTING

CROSS REFERENCE TO RELATED APPLICATIONS

This patent application claims priority to European Patent Application No. 21198721.9, filed Sep. 24, 2021, which is incorporated herein by reference in its entirety.

BACKGROUND

Field

The present disclosure is directed to a method for diffusion-weighted magnetic resonance imaging of an object, which undergoes a cyclic motion, wherein a first sub-period type of the cyclic motion is predicted for a first acquisition timeframe, wherein the first sub-period type corresponds to one of two or more predefined characteristic types of sub-periods of the cyclic motion. The disclosure is further directed to a corresponding magnetic resonance imaging system and a computer program product.

Related Art

Magnetic resonance, MR, imaging systems use a strong external magnetic field to align nuclear spins of an object under examination and excite them to precess about the corresponding alignment by means of applying an excitation RF pulse. The precession or the transition of the spins from this excited state to a state with lower energy, respectively, generates an alternating electromagnetic field in response, which can be detected via receiving antennas as an MR signal.

With the aid of magnetic gradient fields, a position encoding can be impressed on the signals, which subsequently allows the received signal to be assigned to a volume element of the object under investigation. The received signal can then be analyzed, for example to provide an image representation of the object under examination.

Diffusion-weighted MR-imaging exploits the diffusion of water molecules in the object, in particular in tissue of a human or animal, due to Brownian motion. Different types of materials or tissues exhibit different respective diffusion coefficients. Therefore, imaging a measure for the spatial variation of diffusion, in particular in terms of an apparent diffusion coefficient (ADC) is particularly useful for tissue characterization, for example tumor characterization.

In MR-imaging, artifacts such as ghosting or signal dropout may arise due to different reasons, for example due to motion of residual fat, cerebrospinal fluid, CSF, or blood. This may for example be caused by respiratory or cardiac motion. In consequence, also an ADC map in diffusion-weighted imaging may suffer from corresponding artifacts.

In the publication R. Frost et al., "3D Multi-Slab Diffusion-Weighted Readout-Segmented EPI with Real-Time Cardiac-Reordered k-Space Acquisition," Magnetic Resonance in Medicine 72:1565-1579 (2014), a three-dimensional extension of a readout-segmented echo-planar imaging sequence for diffusion imaging is presented. It is found that utilizing a pulse oximeter and acquiring central k-space segments in the diastolic cardiac phase could reduce artifacts.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
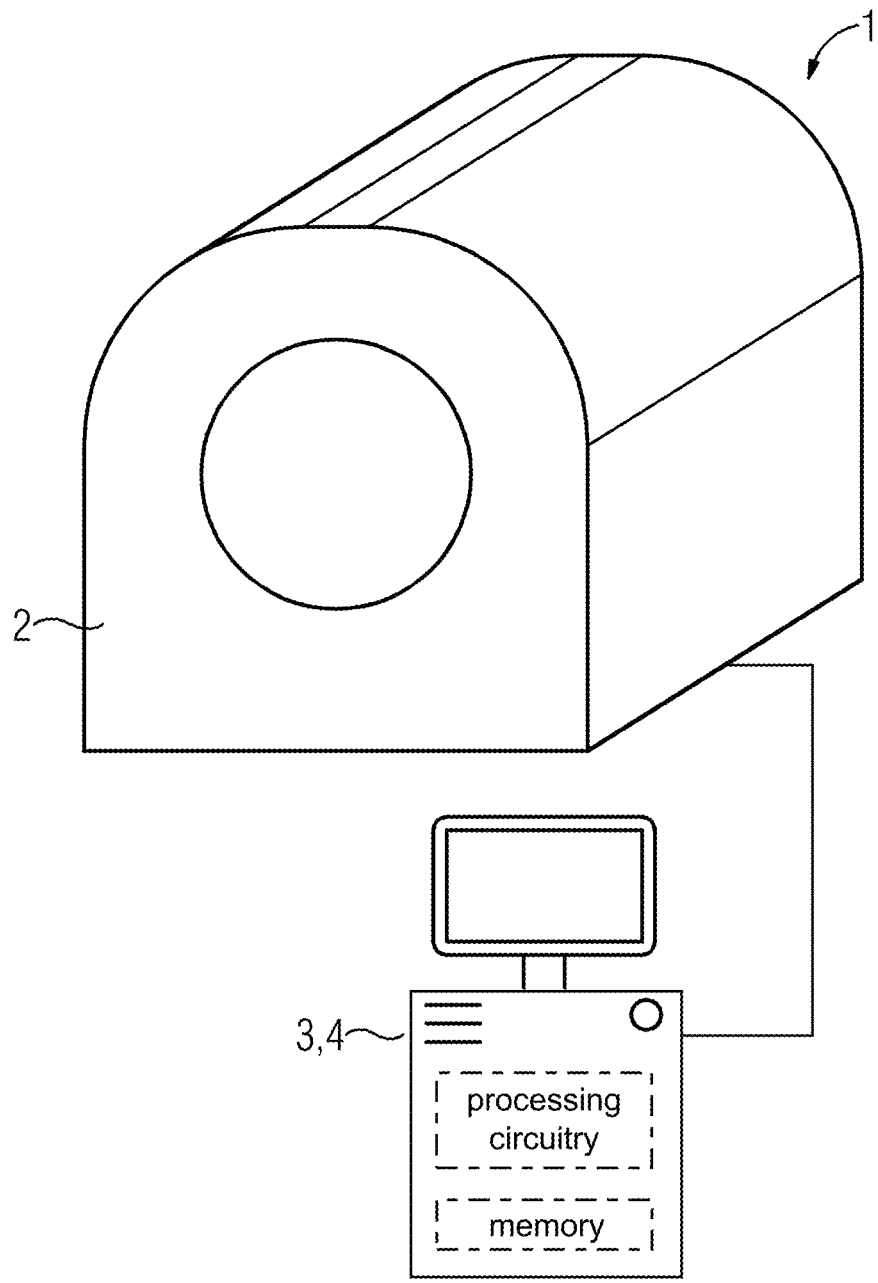
FIG. 1 shows an MR-imaging system according to an exemplary embodiment of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to reduce artifacts in diffusion-weighted MR-imaging.

The disclosure is based on the finding that the extent of artifacts depends, on the one hand, on the amount of diffusion-weighting, which is applied during acquisition and, on the other hand, on the specific timing of the acquisition with respect to characteristic sub-periods of the cyclic motion causing the artifacts. Therefore, a sub-period type of the cyclic motion for an upcoming acquisition timeframe is predicted and the amount of diffusion-weighting for the acquisition is selected depending on the predicted sub-period type.

According to an aspect of the disclosure, a method for diffusion-weighted MR-imaging of an object, which undergoes a cyclic motion during the imaging, is provided. Therein, a first sub-period type of the cyclic motion is predicted, in particular by at least one computing unit, for a first, in particular upcoming, acquisition timeframe. The first sub-period type corresponds to one of two or more predefined characteristic types of sub-periods of the cyclic motion. A first amount of diffusion-weighting is selected, in particular by the at least one computing unit, depending on the determined first sub-period type. A first MR-acquisition is carried out, in particular by an MR-imaging system, during the first acquisition timeframe, wherein a diffusion-weighting according to the first amount of diffusion-weighting is applied during the first acquisition timeframe or, in other words, for the first MR-acquisition. An MR-image representing the imaged part of the object is generated, in particular by the at least one computing unit, depending on MR-data, which includes a first MR-dataset obtained as a result of the first MR-acquisition.

In other words, the MR-image is generated depending on the first MR-dataset and optionally depending on further datasets, which may, in particular, be obtained as respective results of further MR-acquisitions during further acquisition timeframes and, in particular, for different amounts of diffusion-weighting.

The object is, in particular, a part of a human or animal body, for example a head or brain of the human or animal. However, the object may also be another object containing a liquid, such as water, which undergoes a cyclic motion with characteristic sub-periods.

Carrying out an MR-acquisition, in particular the first MR-acquisition, includes the application of an RF pulse, wherein RF stands for radio frequency, in particular a 180°-pulse, and detecting a resulting MR-signal by means of one or more receiving antennas of the MR-imaging system. The MR-data, in particular the first MR-dataset, is obtained based on the detected MR-signal.

In case of diffusion-weighting imaging, at least one magnetic field gradient, also denoted as diffusion gradient lobe in the following, is applied symmetrically on either side of the RF pulse. In this way, stationary water molecules may be distinguished from moving water molecules. While stationary water molecules acquire the same phase information by the diffusion gradient lobes prior to and after the RF pulse, moving water molecules obtain slightly different phases prior to and after the RF pulse. Therefore, the further they move between the diffusion gradient lobes, the more the moving water molecules dephase. Therefore, the further they move, the less MR-signal they cause.

Diffusion-weighting MR-imaging uses, in general, different amounts of diffusion-weighting in different acquisition timeframes to generate an MR-image, in particular an ADC map, which represents the spatial distribution of the apparent diffusion coefficient.

The amount of the diffusion-weighting may be given by the so-called b-value, which may, for example, be defined as $$b = \gamma^2 G^2 \delta^2 (\Delta - \delta/3).$$

Therein, $\gamma$ represents the gyromagnetic ratio, G denotes the amplitude of the diffusion gradient lobes, $\delta$ denotes the duration of the diffusion gradient lobes and $\Delta$ denotes the duration between the pair of diffusion gradient lobes. Therein, it may for example be assumed that the diffusion gradient lobes have an approximately rectangular shape and both have the same amplitude G and duration $\delta$.

Selecting the first amount of diffusion-weighting may be understood such that the first amount of diffusion-weighting, for example the corresponding b-value, is selected from two or more predefined values for the amount of diffusion-weighting, for example for the b-value. In particular, one of the predefined b-values may be b=0, while another predefined value for the b-value may be greater than zero, for example, 1000 s/mm². However, also other values may be used, for example in the range [200 s/mm², 1200 s/mm²]. In a simple implementation, exactly two different b-values are predefined, which include b=0 and a non-zero b-value, for example b=1000 s/mm². According to the determined first sub-period type one of the predefined b-values is selected for the first MR-acquisition.

An acquisition timeframe, in particular the first acquisition timeframe, may be understood to include the application of the diffusion gradient lobes, the application of the RF pulse and the readout of the resulting MR-signal. During an acquisition timeframe, a respective part of the k-space may be sampled.

As indicated above, the MR-data may, apart from the first MR-dataset, comprise respective MR-datasets for a plurality of further acquisition timeframes obtained as a result of respective further MR-acquisitions, which may in part differ by the respective amount of diffusion-weighting applied. The MR-image is then reconstructed based on all of the MR-datasets comprised by the MR-data, for example as an ADC map. Apart from using different b-values for the individual MR-acquisitions, also different gradient directions may be applied and/or averaging of different MR-datasets for the same direction and/or the same b-value may be considered.

The cyclic motion of the object may be understood as a motion of the part of the object to be imaged, which is at least approximately periodical. In particular, the cyclic motion comprises the two or more characteristic types of sub-periods, which may for example correspond to different velocities or directions of the motion of the object to be imaged.

The motion of the object to be imaged or the part of the object to be imaged may for example correspond to a motion of tissue, blood or, in particular when the part of the object to be imaged corresponds to the brain of the human or animal, CSF. This motion may be caused, for example, by cardiac motion or respiratory motion. In this case, the cyclic motion may be characterized according to the characteristic types of sub-period of a cardiac cycle or respiratory cycle, respectively. For example, the two or more characteristic types of sub-periods of the cardiac motion may correspond to the systolic sub-period of the cardiac cycle and the diastolic sub-period of the cardiac cycle or parts thereof, respectively. For the respiratory cycle, the two or more characteristic types of sub-periods may, for example, include an exhaling period, an inhaling period or a plateau phase between inhaling and exhaling, for example.

The sub-period type may be predicted in different ways. For example, a sensor system may be used to measure a quantity which is affected by the cyclic motion in a characteristic manner. The sensor system may for example include a pulse oximeter system, an ECG system or a pilot tone sensor system. By monitoring the corresponding measured quantity, the temporal positions and durations of the individual sub-periods of different sub-period types may be identified and correspondingly extrapolated or predicted for future acquisition periods.

On the other hand, MR-signals and corresponding MR-data themselves inherently contain the information regarding the cyclic motion and the corresponding sub-period types. Therefore, MR-signals or MR-data, which are acquired previously, for example in terms of a navigator scan or a previous MR-acquisition period, may be analyzed by means of a suitable algorithm by the at least one computing unit in order to predict the first sub-period type. To this end, for example, a computer algorithm, which is trained based on machine learning, for example an artificial neural network, may be used for the prediction.

By means of the method according to the disclosure it becomes possible to choose the first amount of diffusion-weighting according to the first sub-period type such that the negative impact of the cyclic motion, in particular ghosting artifacts due to the cyclic motion, may be avoided or reduced. For example, it has been found that artifacts are the more pronounced the smaller the amount of diffusion-weighting is, since for higher b-values, the dephasing due to the diffusion gradients also reduces the ghosting artifacts. On the other hand, certain sub-period types of the cyclic motion may involve less motion of tissue, CSF et cetera and/or less pronounced artifacts than others.

In case of a cardiac cycle, it has been found that artifacts mainly arise during the systolic sub-period and not or hardly during the diastolic sub-period. Therefore, in this case, a lower amount of diffusion-weighting, for example b=0, may be used during the diastolic sub-period and a higher amount of diffusion-weighting may be used during the systolic sub-period. In this way, the influence of the cyclic motion and the corresponding artifacts may be reduced in a systematic manner. However, also different timing schemes, which relate the amount of diffusion-weighting to the identified sub-period type may be employed.

According to at least one implementation of the method according to the disclosure, a second sub-period type of the cyclic motion is predicted, in particular by the at least one computing unit, for a second, in particular upcoming, acquisition timeframe. Therein, the second sub-period type differs from the first sub-period type. A second amount of diffusion-weighting is selected, in particular by the at least one computing unit, depending in the second sub-period type. The second amount of diffusion-weighting differs from the first amount of diffusion-weighting. A second MR-acquisition is carried out, in particular by the MR-imaging system, during the second acquisition timeframe, wherein a diffusion-weighting according to the second amount of diffusion-weighting is applied to the second acquisition timeframe or during the second MR-acquisition, respectively. The MR-data includes a second MR-dataset, which is obtained as a result of the second MR-acquisition. In other words, the MR-image is generated depending on the first MR-dataset and the second MR-dataset.

In particular, the b-value according to the first amount of diffusion-weighting may be zero, and the b-value according to the second amount of diffusion-weighting may be greater than zero or vice versa.

In the same way, further MR-acquisitions may be carried out according to the first amount of diffusion-weighting during respective further acquisition timeframes, which correspond to the first sub-period type. The corresponding further MR-datasets may be averaged to generate the MR-image.

The same holds for further MR-acquisitions according to the second amount of diffusion-weighting during further MR-acquisition timeframes according to the second sub-period type. In an exemplary embodiment, averaging may also be performed. Furthermore, in order to avoid effects due to anisotropy, different spatial directions of the diffusion gradient lobes may be applied during different respective MR-acquisitions for the non-zero b-value.

According to an exemplary embodiment, the MR-image is generated as an ADC map depending on all MR-datasets comprised by the MR-data including the first MR-dataset and the second MR-dataset. For generating the ADC map based on the available MR-datasets or the MR-data, respectively, known methods may be used for combining the MR-datasets of different b-values and gradient directions.

According to an exemplary embodiment, a monitoring MR-scan is carried out prior to the first acquisition timeframe and the first sub-period type is predicted depending on monitoring MR-data obtained as a result of the monitoring MR-scan, in particular by the at least one computing unit.

The same holds, in respective implementations, analogously for the second acquisition timeframe and the prediction of the second sub-period type.

The monitoring MR-scan may be any MR-scan, which is affected by the cyclic motion and therefore may be used to monitor the cyclic motion for characterizing the cyclic motion and in consequence for predicting the sub-period type. The monitoring scan may be part of a previous MR-acquisition or may correspond to a navigator scan. The navigator scan may be used for other purposes as well so that no additional acquisition time is necessary for the navigator scan. However, also a dedicated monitoring scan, which is not used for other purposes may be used.

In an exemplary embodiment, the monitoring MR-scan, for example the navigator scan, may sample one or more k-space lines, close to the center of the k-space, in order to be able to extract characteristic signatures of the cyclic motion in the monitoring MR-data. By using the monitoring MR-data for predicting the sub-period types, it may be avoided that additional sensor systems have to be used. This saves costs and efforts for implementing the additional sensor systems and/or equipping the patient with the sensor and also may avoid corresponding measurement inaccuracies.

The monitoring scan is carried out prior to the first acquisition timeframe and therefore, in particular, prior to the application of the gradient diffusion lobes. Therefore, for a non-zero b-value, a higher signal intensity may be achieved during the monitoring MR-scan since the respective spins are not dephased due to the gradient application.

In particular, for two successive acquisition timeframes, say an n-th and an (n+1)-th acquisition timeframe, the monitoring MR-scan may be carried out between the two acquisition timeframes. Therefore, the sub-period type of the (n+1)-th acquisition timeframe may be predicted based on the monitoring MR-data. Therefore, a particularly short time between the prediction of the sub-period type and the corresponding MR-acquisition may be achieved. However, in other implementations, the monitoring MR-scan may also be used to predict the sub-period type of a later acquisition timeframe, in particular an (n+2)-th acquisition timeframe following the (n+1)-th acquisition timeframe, which may allow for an increased accuracy of the prediction.

According to an exemplary embodiment, carrying out the first MR-acquisition, in particular applying the diffusion-weighting according to the first amount of diffusion-weighting, comprises applying at least two diffusion gradient lobes, which implement the diffusion-weighting, according to the first amount of diffusion-weighting.

According to an exemplary embodiment, the at least two diffusion gradient lobes comprise a first diffusion gradient lobe and a second diffusion gradient lobe, which have the same lobe duration and the same lobe amplitude and may for example have an approximately rectangular pulse shape. The first diffusion gradient lobe is applied prior to the application of the RF pulse and the second diffusion gradient lobe is applied after the RF pulse, wherein the first and the second diffusion gradient lobe are arranged symmetrically with respect to the RF pulse.

According to an exemplary embodiment, the monitoring MR-scan is carried out prior to the at least two diffusion gradient lobes.

According to an exemplary embodiment, a trained machine trainable algorithm is applied to input data, which depends on the monitoring MR-data, in order to predict the first sub-period type.

In particular, the first sub-period type may be considered as a result of the application of the machine trainable algorithm to the input data.

In this way, a particularly reliable and fast prediction of the first sub-period type is possible.

The machine trainable algorithm may be considered as a computer algorithm, which has an architecture, which is trainable and has been trained by means of machine learning. The machine trainable algorithm may for example comprise an artificial neural network, for example a convolutional neural network, CNN.

The training of the machine trainable algorithm may be carried out according to a known training method, for example by using respective annotated sets of training data for the monitoring MR-data, wherein the annotation corresponds to the actual sub-period type during which the training data is acquired.

Also, in order to predict the second sub-period type or other sub-period types for other MR-acquisition timeframes, the trained machine trainable algorithm may be applied to respective input data depending on the respective monitoring MR-data.

According to an exemplary embodiment, a measurement quantity, which depends on the cyclic motion is measured, for example, repeatedly and/or during a corresponding measurement timeframe, prior to the first acquisition timeframe by means of a sensor system in order to generate a sensor dataset representing the measured measurement quantity. The first sub-period type is predicted by the at least one computing unit depending on the sensor dataset.

The same holds analogously for the second sub-period type and further sub-period types of further acquisition timeframes, as far as applicable.

The sensor system may, for example, comprise a system for electrocardiography, ECG, which is attached to the human or animal representing the object. In this way, in case the cyclic motion corresponds to the cardiac motion, the individual sub-period types may be directly identified from the ECG, which may allow for a particularly accurate prediction of the sub-period types in case the cyclic motion corresponds to a cardiac motion.

The sensor system may, alternatively or in addition to the ECG system, comprise a pulse oximeter, which is attached to the object, such that the measured quantity corresponds to a blood oxygen saturation of the human or animal representing the object. In this way, a reliable detection and prediction of cardiac and/or respiratory cycles may be achieved.

The sensor system may also comprise a pilot tone sensor system.

The pilot tone sensor system may comprise a pilot tone generator, which generates an electromagnetic wave with a defined frequency or frequency spectrum or generates another electromagnetic, electric or magnetic field with a defined characteristic. The presence and position of the object in the respective field affect the field, which may in turn be measured by means of a detector coil. Therefore, also the cyclic motion, for example the cardiac motion or the respiratory motion, may be detected in this way.

According to an exemplary embodiment, at least one first reference MR-scan is carried out by using two or more MR-acquisition antennas without applying a diffusion-weighting, in particular with a b-value equal to zero, wherein the at least one first reference MR-scan achieves a complete k-space sampling and wherein the at least one first reference MR-scan is carried out during at least one respective first reference period corresponding to the first sub-period type of the cyclic motion. At least one second reference MR-scan is carried out by using the two or more MR-acquisition antennas without applying a diffusion-weighting, in particular with the b-value equal to zero, wherein the at least one second reference MR-scan achieves a k-space under-sampling and wherein the at least one second reference MR-scan is carried out during at least one respective second reference period corresponding to the first sub-period type of the cyclic motion. A relation, in particular a linear relation, between the first reference MR-data obtained as a result of the at least one first reference MR-scan and second reference MR-data obtained as a result of the at least one second reference MR-scan is determined. The MR-image is generated depending on the MR-data and the determined relation.

In particular, the MR-data also achieves under-sampling of the k-space in the same way as the at least one second reference MR-scan.

In other words, a parallel imaging scheme, for example a GRAPPA-based imaging, an SMS-based imaging, et cetera may be implemented in this way. Therein, the previously determined relation between the under-sampled and the completely sampled k-space data is exploited at a later stage to reconstruct the MR-image. While the reference MR-scans are carried out without applying diffusion-weighting, they are carried out during the first sub-period type of the cyclic motion in order to assure that the first MR-dataset may be processed correctly by using the relation.

In the same way, further first and further second reference MR-scans may be carried out during respective reference periods corresponding to the second sub-period type and a corresponding further relation between the individual reference MR-datasets may be determined, which may then be used to reconstruct the MR-image in combination with the second MR-dataset.

In an exemplary embodiment, for an acceleration factor, which is equal to or greater than 2, the acquisition of the at least first reference scan is performed in a segmented manner. In an exemplary embodiment, the acceleration factor may be equal to or greater than 3. A number of segments is given by the acceleration factor, wherein each segment corresponds to a respective group of lines in the k-space. When all segments have been acquired, the respective parts of the first reference MR-data are combined to obtain the first reference MR-data. Therein, each of the segments is acquired during a respective segment period corresponding to the first sub-period type of the cyclic motion.

In this way, the effect of the cyclic motion on the first reference MR-data, and in consequence on the relation between the first reference MR-data and the second reference MR-data, is particularly small.

According to an exemplary embodiment, the object is a body part of a human or an animal, and the cyclic motion corresponds to a cardiac motion of the human or animal. The two or more characteristic sub-types comprise a diastolic sub-period of the cardiac motion and a systolic sub-period of the cardiac motion. Alternatively, the two or more characteristic sub-types may comprise a part of the diastolic sub-period and a part of the systolic sub-period of the cardiac motion.

According to an exemplary embodiment, the first amount of diffusion-weighting corresponds to a b-value of zero, if the first sub-period type corresponds to the diastolic sub-period.

According to an exemplary embodiment, the first amount of diffusion-weighting corresponds to a b-value, which is greater than zero, preferably equal to or greater than 200 $s/mm^2$, for example equal to or greater than 800 $s/mm^2$, if the first sub-period type corresponds to the systolic sub-period.

For example, the second amount of diffusion-weighting corresponds to a b-value of zero, if the second sub-period type corresponds to the diastolic sub-period and/or the first amount of diffusion-weighting corresponds to a b-value, which is greater than zero, preferably equal to or greater than 200 s/mm$^2$, for example equal to or greater than 800 s/mm$^2$, if the second sub-period type corresponds to the systolic sub-period.

Therein, however, it has to be noted that the first sub-period type differs from the second sub-period type. In other words, if the first sub-period type corresponds to the diastolic sub-period and the second sub-period type corresponds to the systolic sub-period, the first amount of diffusion-weighting corresponds to the b-value equal to zero, and the second amount of diffusion-weighting corresponds to a b-value which is greater than zero.

According to an exemplary embodiment, the object is the body part of a human or an animal, and the cyclic motion corresponds to a respiratory motion of the human or animal.

In particular, the two or more characteristic types of sub-periods comprise at least a part of an inhaling sub-period and at least a part of an exhaling sub-period.

According to an exemplary embodiment, the method is implemented according to an echo planar imaging scheme, in particular according to an echo planar parallel imaging scheme.

According to a further aspect of the disclosure, an MR-imaging system for diffusion-weighted MR-imaging of an object, which undergoes a cyclic motion, is provided. In an exemplary embodiment, the MR-imaging system may include an MR-scanner and at least one computing unit (e.g. controller), which is configured to predict a first sub-period type of the cyclic motion for a first acquisition timeframe, wherein the first sub-period type corresponds to one or more predefined characteristic types of sub-periods of the cyclic motion. In an exemplary embodiment, the at least one computing unit may be configured to select a first amount of diffusion-weighting depending on the first sub-period type. The MR-scanner may be configured to apply a diffusion-weighting according to the first amount of diffusion-weighting and to carry out a first MR-acquisition during the first acquisition timeframe. The at least one computing unit may be configured to generate an MR-image of the object depending on the MR-data including a first MR-dataset obtained, in particular by means of the MR-scanner, as a result of the first MR-acquisition.

The MR-scanner may, for example, comprise a field magnet for generating a homogeneous ground field, one or more gradient coils for generating magnetic field gradients, in particular the diffusion gradient lobes, one or more RF-sending antennas for generating respective RF-excitation pulses or RF-refocusing pulses and/or one or more receiving antennas for detecting respective MR-signals in response to the excitation.

The MR-scanner may also comprise a controller, which is configured to control said individual components and to supply power and/or RF-signals to carry out the MR-imaging. The controller of the MR-scanner may be a part of the at least one computing unit or may be separate from the at least one computing unit.

Further implementations of the MR-imaging system according to the disclosure following directly from the various implementations of the method according to the disclosure and vice versa. In particular, an MR-imaging system according to the disclosure may be configured to carry out a method according to the disclosure or carries out such a method.

According to a further aspect of the disclosure, a computer program product comprising instructions is provided. When the instructions are executed by an MR-imaging system according to the disclosure, in particular by the at least one computing unit and/or the controller, the instructions cause the MR-imaging system to carry out a method according to the disclosure. The computer program product may be embodied on a computer-readable storage medium (e.g. memory).

According to a further aspect of the disclosure, also a computer-readable storage medium storing a computer program according to the disclosure is provided.

If it is mentioned in the present disclosure that a component of the MR-imaging system according to the disclosure, in particular the at least one computing unit of the MR-imaging system, is adapted, configured or designed to, et cetera, to perform or realize a certain function, to achieve a certain effect or to serve a certain purpose, this can be understood such that the component, beyond being usable or suitable for this function, effect or purpose in principle or theoretically, is concretely and actually capable of executing or realizing the function, achieving the effect or serving the purpose by a corresponding adaptation, programming, physical design and so on.

A computing unit may in particular be understood as a data processing device, which comprises processing circuitry. The computing unit may therefore in particular process data to perform computing operations. This may also include operations to perform indexed accesses to a data structure, for example a look-up table, LUT.

In particular, the computing unit may include one or more computers, one or more microcontrollers, and/or one or more integrated circuits, for example, one or more application-specific integrated circuits, ASIC, one or more field-programmable gate arrays, FPGA, and/or one or more systems on a chip, SoC. The computing unit may also include one or more processors, for example one or more microprocessors, one or more central processing units, CPU, one or more graphics processing units, GPU, and/or one or more signal processors, in particular one or more digital signal processors, DSP. The computing unit may also include a physical or a virtual cluster of computers or other of said units.

In various embodiments, the computing unit includes one or more hardware and/or software interfaces and/or one or more memory units.

A memory unit may be implemented as a volatile data memory, for example a dynamic random access memory, DRAM, or a static random access memory, SRAM, or as a non-volatile data memory, for example a read-only memory, ROM, a programmable read-only memory, PROM, an erasable read-only memory, EPROM, an electrically erasable read-only memory, EEPROM, a flash memory or flash EEPROM, a ferroelectric random access memory, FRAM, a magnetoresistive random access memory, MRAM, or a phase-change random access memory, PCRAM.

Further features of the disclosure are apparent from the claims, the figures and the figure description. The features and combinations of features mentioned above in the description as well as the features and combinations of features mentioned below in the description of figures and/or shown in the figures may be comprised by the disclosure not only in the respective combination stated, but also in other combinations. In particular, embodiments and combinations of features, which do not have all the features of an originally formulated claim, are also comprised by the disclosure. Moreover, embodiments and combinations of features which go beyond or deviate from the combinations of features set forth in the recitations of the claims are comprised by the disclosure.

In the following, the disclosure will be explained in detail with reference to specific exemplary implementations and respective schematic drawings. In the drawings, identical or functionally identical elements may be denoted by the same reference signs. The description of identical or functionally identical elements is not necessarily repeated with respect to different figures.

FIG. 1 shows schematically an exemplary implementation of an MR-imaging system 1 according to the disclosure.

The MR-imaging system 1 comprises an MR-scanner 2 and a controller 3 for controlling the MR-scanner 2. Furthermore, the MR-imaging system 1 comprises a computing unit (computer) 4 coupled to the controller 3 and/or to the MR-scanner 2. Alternatively, the computing unit 4 may comprise the controller 3 or vice versa. The MR-imaging system 1 may also comprise a memory storage unit (memory) storing a computer program according to the disclosure. In an exemplary embodiment, the controller 3 and/or computing unit 4 include processing circuitry that is configured to perform one or more respective functions/operations of the controller 3 and/or computing unit 4.

The MR-imaging system 1 may be used to carry out a method for diffusion-weighted imaging according to the disclosure. In particular, the computing unit 4 may execute the computer program according to the disclosure to cause the MR-imaging system 1 to carry out the method.

In general, diffusion-weighted imaging may be considered to exploit the attenuation of the respective MR-signal, in particular corresponding to T2*, based on the diffusion of water molecules in the region to be imaged. The more diffusion occurs, the further a water molecule may move within a given period of time, which suppresses the T2*-signal. For example, cerebrospinal fluid, CSF, comprises water, which may diffuse rather easily so that the respective image regions may appear dark or black. On the other hand, water within tissues may not move as easily. Thus, a respective contrast may be achieved.

For diffusion-weighted imaging, one or more b0-images may be obtained. These are MR-datasets acquired without applying diffusion-weighting or, in other words, with b=0, where $$b=\gamma^2 G^2 \delta^2 (\Delta - \delta/3).$$

Therein, $\gamma$ denotes the gyromagnetic ratio, G denotes the amplitude of the diffusion gradient lobes, $\delta$ denotes their respective duration and $\Delta$ denotes the duration between them.

Then one or more images with b>0, in particular b≥200 s/mm$^2$, for example b=500 s/mm$^2$ or b=800 s/mm$^2$ or b=1000 s/mm$^2$ are obtained, which may be denoted as b500-images, b800-images, b1000-images et cetera, respectively, or by b>0-images in general. In particular, respective b>0-images may be obtained for different, in particular three or more, spatial directions of the diffusion gradients.

These images may be combined to generate maps, which do not contain directional information. To generate isotropic maps, a mean value of the direction-specific b>0-images may be calculated. An apparent diffusion coefficient (ADC) map may be obtained by evaluating the logarithm of said mean and setting it into relation to the b0-images.

In the following, the function of the MR-imaging system 1 is explained in more detail with respect to several implementations of methods according to the disclosure with reference to FIG. 2 to FIG. 4.

Figure 2:
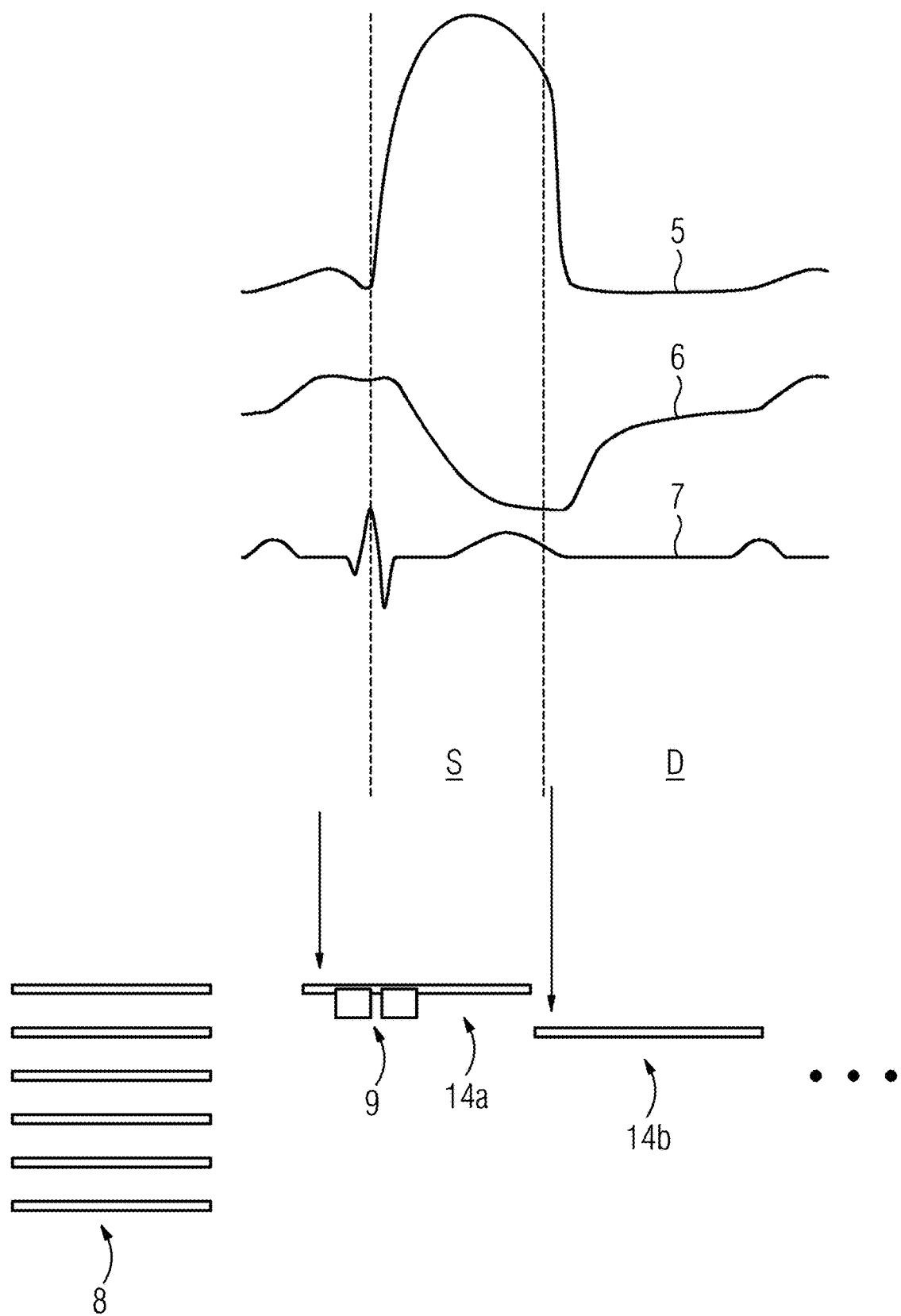
FIG. 2 shows part of a cardiac cycle and a respective timing of acquisition timeframes according to an exemplary embodiment of the disclosure.

For example, a first sub-period type S of the cyclic motion is predicted by the computing unit 4 for a first acquisition timeframe 14a, wherein the first sub-period type S corresponds to one of two or more predefined characteristic types of sub-periods of the cyclic motion, as depicted schematically in FIG. 2. A first non-zero b-value is selected by the computing unit 4 depending on the first sub-period type S and a first MR-acquisition is carried out by the MR-scanner 2 during the first acquisition timeframe 14a, wherein a diffusion gradient lobes 9 according to the first b-value are applied.

Furthermore, a second sub-period type D of the cyclic motion is predicted by the computing unit 4 for a second acquisition timeframe 14b, wherein the second sub-period type D corresponds to another one of the two or more predefined characteristic types. The b-value is set to zero and a second MR-acquisition is carried out by the MR-scanner 2 during the second acquisition timeframe 14b.

The procedure may be repeated as described to acquire all slices 8 necessary for the desired imaging result.

An MR-image representing the object is generated by the computing unit 4 depending on MR-data including a first MR-dataset obtained as a result of the first MR-acquisition and a second MR-dataset obtained as a result of the second MR-acquisition.

In the example shown in FIG. 2, the cyclic motion corresponds to a cardiac motion. The first sub-period type S is therefore a systolic sub-period and the second sub-period type D is a diastolic sub-period. For a better visualization, the ventricular pressure 5, the ventricular volume 6 and a hypothetic ECG-curve 7 are shows schematically as a function of time.

In particular, only b>0-images are acquired during systolic sub-periods, while b0-images are acquired only during diastolic sub-periods. Consequently, ghosting artifacts due to the cardiac motion are avoided or reduced since these occur predominantly for acquisitions during the systolic sub-periods. Due to the non-zero b-value, however, they are suppressed. It is noted that, in particular once all required b0-images are acquired, remaining b>0-images may also be acquired during systolic sub-periods.

The monitoring of the cardiac phase may be performed by using an external sensor (not shown), for example an ECG, a pulse oximeter or a pilot tone sensor. A pilot tone sensor would be particularly beneficial, as no additional patient preparation effort is necessary.

Alternatively, or in addition, the monitoring may be performed utilizing navigator scans or image-scan-inherent information of earlier MR-acquisitions. The latter would be particularly beneficial, as no additional hardware would be needed at all.

Figure 3:
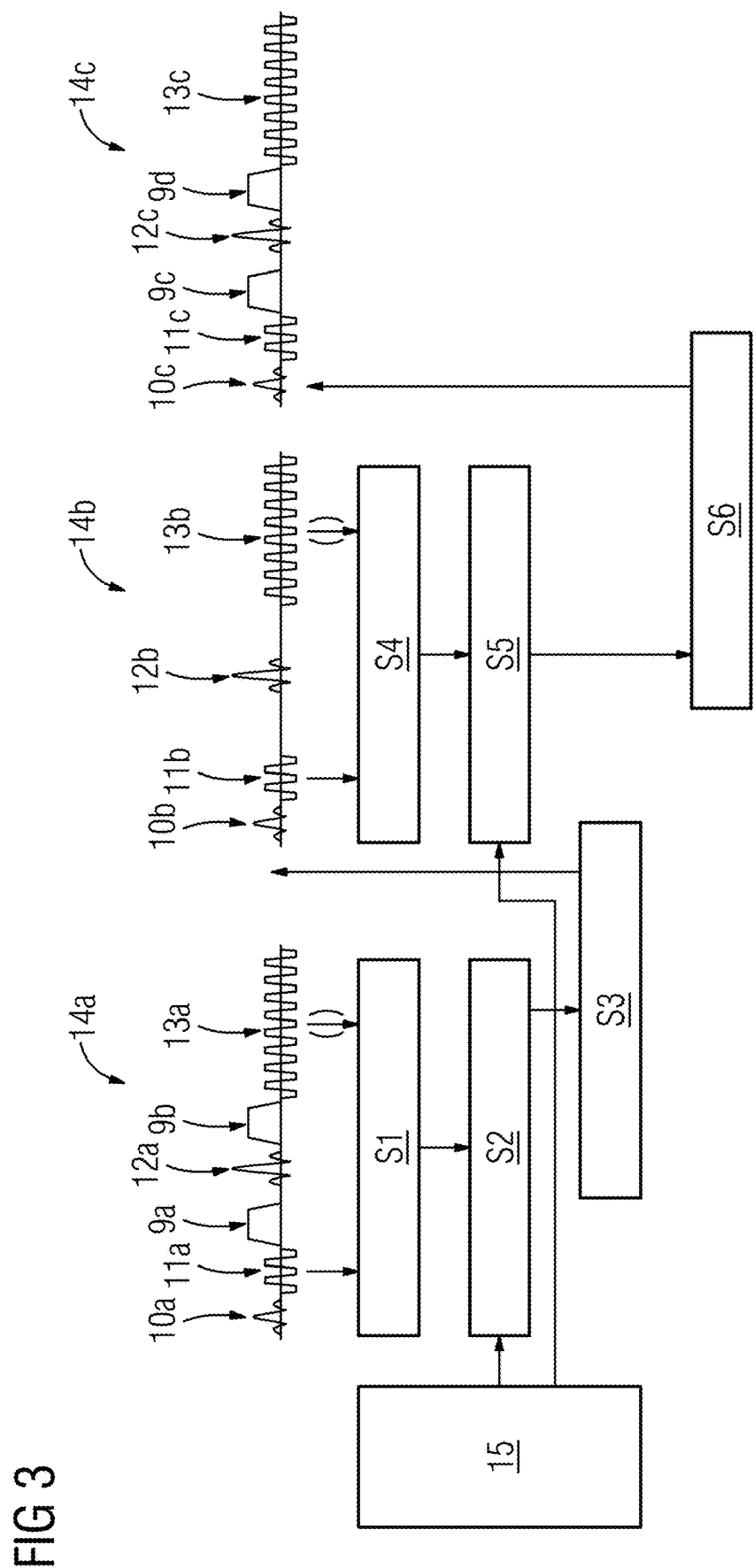
FIG. 3 is a flowchart of a method according to an exemplary embodiment of the disclosure.

A flow diagram of a further exemplary implementation of a method according to the disclosure, which utilizes navigator data is schematically shown in FIG. 3. The scheme shows three consecutive acquisitions timeframes 14a, 14b, 14c, during each of which a respective excitation RF-pulse 10a, 10b, 10c is applied and a respective navigator signal 11a, 11b, 11c is obtained. After the navigator scans, a respective RF-refocusing pulse 12a, 12b, 12c, in particular a respective 180°-pulse, is applied and a respective MR-signal 13a, 13b, 13c is obtained. Prior to and after the refocusing pulse 12a, 12b, 12c, respective diffusion gradient lobes 9a, 9b, 9c, 9d are applied according to the selected b-value. For example, the b-value may be 1000 s/mm$^2$ for the first and the third acquisitions timeframes 14a, 14c and zero for the second acquisition timeframe 14b.

In step S1, the computing unit 4 obtains the first navigator signal 11a and determines in step S2 whether a diastole is likely to occur in the second acquisition timeframe 14b. Since this is the case in the present example, the computing unit 4 sets the b-value to zero for the second acquisition timeframe 14b in step S3. Optionally, the computing unit 4 may also consider historic information 15 regarding previous cardiac cycles, which may be obtained from previous navigator scans, previous MR-acquisitions and/or from sensor data, for the decision in step S2. This may be beneficial to predict the durations of the sub-periods to be expected and, consequently, to predict the available duration for the second acquisition timeframe 14b to decide whether enough time is available to carry out an acquisition with b=0 during a diastole or not.

In the analogous manner, the computing unit 4 obtains the second navigator signal 11b and determines in step S5 whether a diastole is likely to occur in the third acquisition timeframe 14c. Since this is not the case in the present example, the computing unit 4 sets the b-value to the non-zero value, for example 1000 s/mm$^2$, for the third acquisition timeframe 14c in step S6. Optionally, the computing unit 4 may also consider the historic information 15 for the decision in step S5.

Since a time required for the decision to select the b-value accordingly may be larger than the time between the end of the navigator scan and the subsequent application of the diffusion gradients, the embodiment shown in the example of FIG. 3 does not apply the prediction of the cardiac phase for the immediately following acquisition but for the next one. However, in other implementations, the prediction may also be done for immediately following acquisition.

Figure 4:
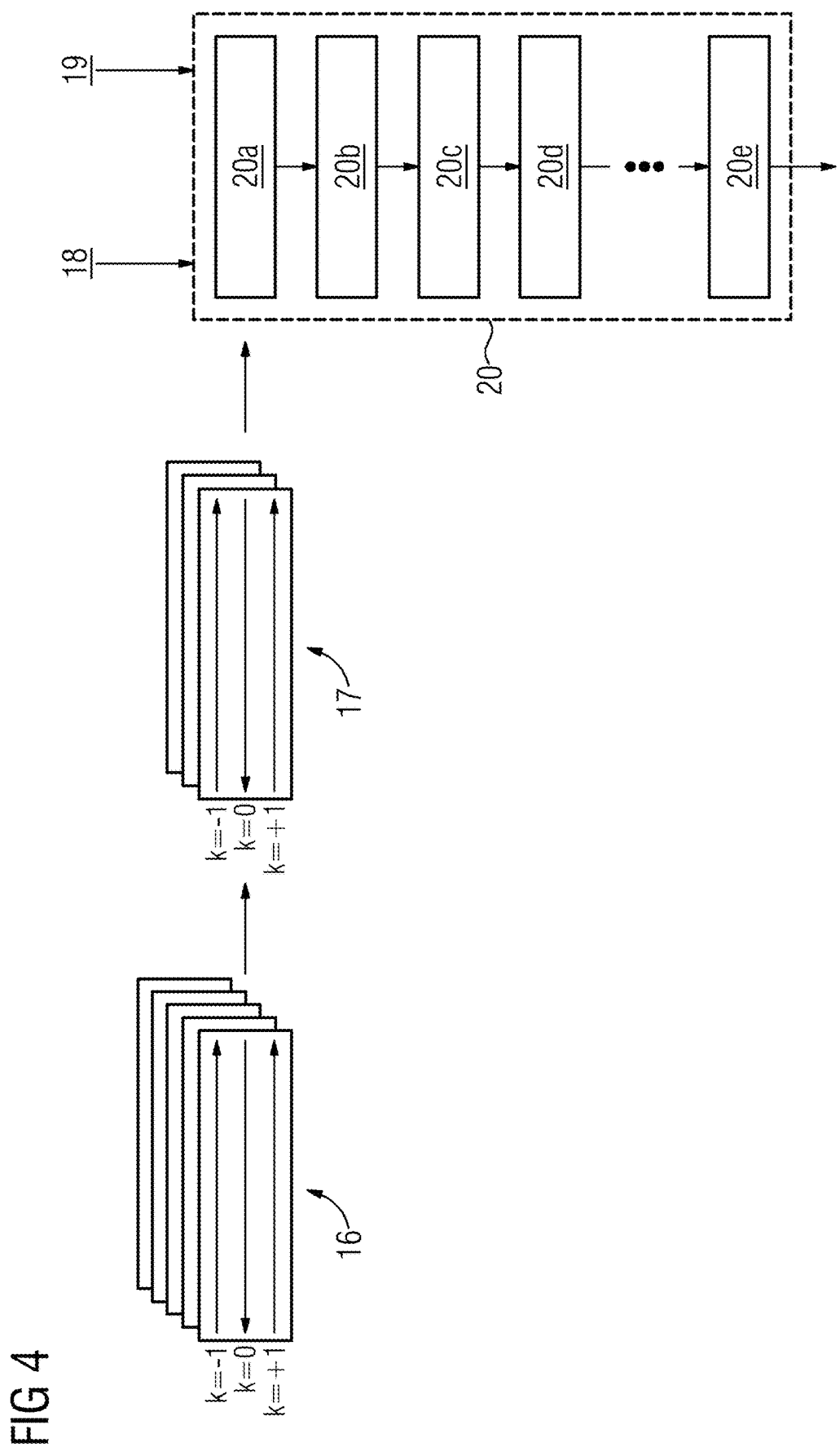
FIG. 4 shows an artificial neural network for a method according to an exemplary embodiment of the disclosure.

In order to determine whether a diastole is approaching or a systole is to be expected, the computing unit may for example apply a correspondingly trained neural network 20, as shown schematically in FIG. 4.

In particular, FIG. 4 shows a schematic processing pipeline of a neural network 20, which may be implemented as a convolutional neural network with layers 20a to 20e. For example, the layer 20a may correspond to a convolutional layer, the following layer 20b may implement a rectifying linear unit, ReLU, function and maximum pooling, the following layer 20c may again be a convolutional layer and the following layer 20d may again implement a ReLU function and maximum pooling. An output layer 20e may correspond to a fully connected layer.

The input data for the neural network 20 may comprise a channel compressed navigator data 17 of the respective complex navigator data 16 or other central k-space data, which is compressed to a fixed number of channels, for example four channels, in the channel direction. Furthermore, the input could optionally comprise the time or fraction of time 18 since the last systole and navigator data 19 from either the same slice at a previous time point or of slices acquired shortly before.

Instead of a convolutional neural network shown here, also a more advanced architecture, for example based on a ResNet can be utilized as well. Alternatively, or in addition, also a recurrent neural network, RNN may be utilized to make better use of the additional navigator data 19.

As described, in particular with respect to the figures, the disclosure allows to reduce or avoid artifacts in diffusion weighted MR-imaging.

In particular echo planar imaging, especially in conjunction with parallel imaging, may suffer from residual fat and/or CSF ghost artifacts. These artifacts are typically only present in b0 images as the fat/CSF is dephased for higher b-values. This leads to additional artifacts in the ADC maps.

One of the supposed root causes is a mismatch of the signal evolution between the fully sampled calibration scan and the under-sampled imaging scan, which may alter the effective echo spacing and therefore the amount of spatial distortions.

Herein, methods are proposed, which can mitigate the aforementioned artifacts by performing a dynamic scheduling of the diffusion-weighted scans to be acquired. To this end, for example the cardiac state may be monitored in respective embodiments and b0-encoded slices bay be obtained during the diastolic phase whenever possible. In some implementations, navigator scans which are already acquired for other purposes are analyzed, for example by means of a neural network, to avoid the usage of additional hardware.

In particular, based on the expected cardiac phase, the slice is either acquired as a b0-scan (during a diastolic phase) or as a diffusion-weighted scan (during a systolic phase). As soon as all b0-scans are acquired, all remaining diffusion weighted scans may be acquired in any cardiac phase.

Depending on the exact timing, a few extra acquisitions might be necessary to acquire all remaining data. Due to the extra acquisitions, some data is going to be acquired more often than originally prescribed. This can then optionally be averaged with data with identical diffusion-weighting and gradient direction to increase the total SNR. In an alternative embodiment, if an extension of measurement time is not desired, still missing b0-acquisitions can be acquired in any cardiac phase as soon as the number of remaining repetitions is equal to the maximum of the number of missing b0-scans per slice. This approach keeps the measurement time constant. The number of allowed extra acquisitions can also be fixed at the beginning of the acquisition, which would lead to a combination of both described methods.

In some embodiments, the reordering of the acquired scans can also comprise reference scans, for example for GRAPPA, SMS, dynamic field correction et cetera. This will further improve image quality; however, the respective image reconstruction steps can only start as soon as all respective reference data is available.

According to the one or more embodiments, the method can be extended to the RESOLVE sequence by determining the cardiac phase either from the FID navigator sampled directly after the excitation of a slice or from the navigator scan of the preceding slice acquisition. The neural networks described above may be applied to these data as well.

The method can also be adapted to be sensitive to other physiological effects as well apart from the cardiac motion. For example, the rescheduling could also happen based on the respiratory cycle. This could be beneficial especially in spine imaging and would not be limited to echo planar imaging but could be extended, for example, to gradient echo acquisitions where phase effects caused by respiratory motion pose a big problem. The rescheduling could then happen in a way that the transition between adjacent k-space points is as smooth as possible by keeping it similar to the breathing curve.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for diffusion-weighted magnetic resonance (MR) imaging of an object, which undergoes a cyclic motion, comprising:
    determining a first sub-period type of the cyclic motion for a first acquisition timeframe, wherein the first sub-period type corresponds to one of two or more predefined characteristic types of sub-periods of the cyclic motion;
    selecting a first amount of diffusion-weighting based on the first sub-period type;
    performing a first MR-acquisition during the first acquisition timeframe, wherein a diffusion-weighting according to the first amount of diffusion-weighting is applied; and
    generating an MR-image representing the object based on MR-data including a first MR-dataset obtained as a result of the first MR-acquisition.

2. The method according to claim 1, further comprising:
    determining a second sub-period type of the cyclic motion for a second acquisition timeframe, wherein the second sub-period type is different from the first sub-period type;
    selecting a second amount of diffusion-weighting based on the second sub-period type, wherein the second amount of diffusion-weighting is different from the first amount of diffusion-weighting; and
    performing a second MR-acquisition during the second acquisition timeframe, wherein a diffusion-weighting according to the second amount of diffusion-weighting is applied,
    wherein the MR-data includes a second MR-dataset that is obtained as a result of the second MR-acquisition.

3. The method according to claim 1, further comprising:
    performing a monitoring MR-scan prior to the first acquisition timeframe to determining monitoring MR-data,
    wherein the first sub-period type is determined based on the monitoring MR-data.

4. The method according to claim 3, wherein:
    performing the first MR-acquisition comprises applying at least two diffusion gradient lobes, which implement the diffusion-weighting according to the first amount of diffusion-weighting; and
    the monitoring MR-scan is performed prior to the at least two diffusion gradient lobes.

5. The method according to claim 3, further comprising applying a trained machine trainable algorithm to input data based on the monitoring MR-data to predict the first sub-period type.

6. The method according to claim 5, wherein the machine trainable algorithm comprises an artificial neural network.

7. The method according to claim 1, further comprising:
measuring, using a sensor, a measurement quantity, which depends on the cyclic motion, prior to the first acquisition timeframe to generate a sensor dataset,
wherein the first sub-period type is determined based on the sensor dataset.

8. The method according to claim 7, wherein the sensor comprises:
a system for electrocardiography attached to the object;
a pulse oximeter attached to the object; and/or
a pilot tone sensor system.

9. The method according to claim 1, further comprising:
performing at least one first reference MR-scan using two or more MR-acquisition antennas without applying a diffusion-weighting, wherein the least one first reference MR-scan is configured to achieve a complete k-space sampling and wherein the least one first reference MR-scan is performed during at least one respective first reference period corresponding to the first sub-period type of the cyclic motion;
performing at least one second reference MR-scan using two or more MR-acquisition antennas without applying a diffusion-weighting, wherein the least one second reference MR-scan is configured to achieve a k-space under-sampling and wherein the least one second reference MR-scan is performed during at least one respective second reference period corresponding to the first sub-period type of the cyclic motion; and
determining a relationship between first reference MR-data obtained as a result of the at least one first reference MR-scan and second reference MR-data obtained as a result of the at least one second reference MR-scan,
wherein the MR-image is generated based on the MR-data and the determined relationship.

10. The method according to claim 1, wherein:
the object is a body part of a human or an animal, and the cyclic motion corresponds to a cardiac motion of the human or animal; and
the two or more characteristic types of sub-periods comprise at least a part of diastolic sub-period and at least a part of systolic sub-period of the cardiac motion.

11. The method according to claim 10, wherein:
in response to the first sub-period type corresponding to the diastolic sub-period, the first amount of diffusion-weighting corresponds to a b-value of zero; and/or
in response to the first sub-period type corresponding to the systolic sub-period, the first amount of diffusion-weighting corresponds to a b-value greater than zero.

12. The method according to claim 1, wherein the object is a body part of a human or an animal and the cyclic motion corresponds to a respiratory motion of the human or animal.

13. The method according to claim 1, wherein the method is implemented according to an echo planar imaging scheme.

14. A non-transitory computer-readable storage medium with an executable program stored thereon, that when executed, instructs a processor to perform a method for diffusion-weighted magnetic resonance (MR) imaging of an object, which undergoes a cyclic motion, comprising:
determining a first sub-period type of the cyclic motion for a first acquisition timeframe, wherein the first sub-period type corresponds to one of two or more predefined characteristic types of sub-periods of the cyclic motion;
selecting a first amount of diffusion-weighting based on the first sub-period type;
performing a first MR-acquisition during the first acquisition timeframe, wherein a diffusion-weighting according to the first amount of diffusion-weighting is applied; and
generating an MR-image representing the object based on MR-data including a first MR-dataset obtained as a result of the first MR-acquisition.

15. A magnetic resonance (MR) imaging system for diffusion-weighted MR imaging of an object, which undergoes a cyclic motion, the (MR) imaging system comprising:
an MR-scanner; and
a controller configured to:
predict a first sub-period type of the cyclic motion for a first acquisition timeframe, wherein the first sub-period type corresponds to one of two or more predefined characteristic types of sub-periods of the cyclic motion;
select a first amount of diffusion-weighting based on the first sub-period type;
control the MR-scanner to apply a diffusion-weighting according to the first amount of diffusion-weighting and to carry out a first MR-acquisition during the first acquisition timeframe; and
generate an MR-image of the object based on MR-data including a first MR-dataset obtained as a result of the first MR-acquisition.

\* \* \* \* \*